United States Patent [19]

Pomper et al.

[11] Patent Number: 4,764,472

[45] Date of Patent: Aug. 16, 1988

[54] REHYDRATABLE INSTANT ACTIVE DRIED YEAST

[75] Inventors: Seymour Pomper, Stamford; Gary Cole, Ridgefield, both of Conn.; Saul Scheinbach, Bronx, N.Y.

[73] Assignee: Nabisco Brands, Inc., Parsippany, N.J.

[21] Appl. No.: 865,909

[22] Filed: May 13, 1986

Related U.S. Application Data

[63] Continuation of Ser. No. 609,485, May 11, 1984, abandoned.

[51] Int. Cl.$^4$ .......................... C12N 1/18; A23L 1/28
[52] U.S. Cl. ...................................... 435/256; 426/60; 426/62
[58] Field of Search ...................... 426/60, 62; 435/256

[56] References Cited

U.S. PATENT DOCUMENTS

| | | | |
|---|---|---|---|
| 4,160,040 | 7/1979 | Lucz et al. | 426/62 |
| 4,341,871 | 7/1982 | Langejan et al. | 426/62 X |
| 4,370,420 | 1/1983 | Clement et al. | 426/62 X |

Primary Examiner—David M. Naff
Attorney, Agent, or Firm—Richard Kornutik

[57] ABSTRACT

An instant-type active dry yeast is provided which contains from about 0.1% to about 2.0% by weight (dry matter basis) of a material selected from the group consisting of locust bean gum, gum ghatti and mixtures thereof. The instant-type active dry yeast of the invention has a high leavening activity when used in direct addition processes as well as a comparably high leavening activity when employed in processes in which the yeast is first rehydrated prior to its admixture with flour and remaining dough or batter ingredients.

12 Claims, No Drawings

REHYDRATABLE INSTANT ACTIVE DRIED YEAST

This application is a continuation of prior application Ser. No. 609,485, filed May 11, 1984, and now abandoned.

BACKGROUND OF THE INVENTION

The present invention relates to active dry yeast and, more particularly, to instant-type active dry yeast and a method for its preparation.

Yeast supplied to commercial bakeries as well as to consumers is generally available in two forms, i.e., as "compressed yeast" having a moisture content of from about 67 to about 73% or as "active dry yeast" having a moisture content of less than about 10%. Active dry yeast in general has the distinct advantage of being stable over prolonged periods of storage, even at elevated temperatures, but, for most common forms of active dry yeast, generally has a relatively low leavening activity (as compared to compressed yeast) and requires rehydration prior to admixture with dough ingredients in order to develop its activity. As a consequence of the lower activity, larger quantities (on a dry matter basis) of the active dry yeast are needed to obtain leavening equivalent to that obtained using compressed yeast.

In response to these disadvantages of active dry yeast, the art has developed what is known as "instant-type active dry yeast" through use of drying processes employing mild conditions in conjunction with use of yeast strains which are fairly resistant (in the sense of not undergoing a substantial loss of leavening activity) to the drying process. Such instant-type active dry yeasts are characterized (and distinguished from "conventional" active dry yeast) by their high leavening activity in direct addition methods of use, i.e., where the yeast is not rehydrated before admixture with flour and other dough or batter ingredients.

Additional characterizing features of instant-type active dry yeasts are their relatively fine particle size and relatively low moisture content as compared to conventional active dry yeast. The fine particle size contributes to the high direct addition leavening activity of the yeast by promoting its uniform dispersibility throughout the dough or batter ingredients. With respect to moisture content, the high activity of instant-type active dry yeasts, their fine particle size and their generally high protein content have the effect of rendering the dry yeast less stable on storage than a conventional active dry yeast of the same moisture content. As a consequence, production of an instant-type active dry yeast typically will involve drying to a final moisture content lower than generally required for conventional active dry yeast so as to insure adequate storage stability. Generally, the moisture content of instant-type active dry yeast is less than about 6% by weight and most typically on the order of about 4 to 5% by weight. However, in those situations where extended storage stability is not of particular concern or is attained in some manner other than reduction in moisture content, the moisture content of an instant-type active dry yeast can range as high as about 10% by weight.

In those cases where it is desired to produce an instant-type active dry yeast having a relatively low moisture content (e.g., less than about 8%, such as in the typical 4 to 5% range), the drying of the yeast suspension initially involves only the removal of free water (down to a level of about 8% water content by weight); further reduction of the moisture content to the desired low level thereafter involves the elimination of a portion of the bound water from the yeast. This latter phase of moisture reduction can cause severe damage to the yeast cell membrane. To overcome this problem, it is known in the art to conduct the drying of the yeast suspension in the presence of particular lipophilic surfactants or wetting agents such as esters of saturated fatty acids, fatty acid esters of glycerol and fatty acid esters of propylene glycol. These materials have the effect of protecting the yeast cells when the cells are dried to a low moisture content, thereby preserving the desired high direct addition leavening activity of the yeast.

Prior art processes for the production of instant-type active dry yeast are disclosed, for example, in U.S. Pat. Nos. 3,843,800 and 4,218,420 to Langejan (drying of high protein content yeast suspension under controlled conditions of time and temperature with a drying gas), and Canadian Pat. No. 1,075,077, British Patent Specification No. 1,539,211 and U.S. Pat. Nos. 4,346,115, 4,328,250, 4,318,930 and 4,396,632, all to Clement, et al. (disclosing particular yeast strains, propagation processes and controlled drying conditions).

As a result of the fact that instant-type active dry yeasts were developed in response to the low activity of conventional active dry yeast and the need to rehydrate the conventional active dry yeast and the need to rehydrate the conventional active dry yeast in water in order to develop its activity, the "acid test", so to speak, for instant-type active dry yeast has been the leavening activity achieved in direct addition methods of use, and instant-type active dry yeasts are provided to consumers and commercial bakers with the intent that they be employed in direct admixture with flour and other dough or batter ingredients.

It has been found, however, that many consumers and bakers, either as a consequence of simply being steeped in traditional methods and/or because of constraints imposed by arrangement of particular machinery and process streams in existing commercial bakery plants, nevertheless adhere to the practice of first rehydrating the yeast in water before mixing it with flour and other dough or batter ingredients. Surprisingly, it has been found that such practice results in a substantial decrease in the leavening activity of an instant-type active dry yeast (as compared to its use in direct addition processes). Hence, a product touted as being of high activity is, in these cases, perceived by the user as being a step backward. While a yeast manufacturer can make both a conventional active dry yeast and an instant type active dry yeast so as to accommodate the needs of users respectively employing rehydration methods and direct addition methods of yeast utilization, it is of course impossible for the manufacture to control the particular method which the consumer may choose to employ in any given situation.

Accordingly, a need exists for a yeast which eliminates this problem and produces leavening results which meet users' expectations regardless of whether the yeast is utilized with direct addition or rehydration methods.

SUMMARY OF THE INVENTION

It is accordingly an object of the invention to provide an instant-type active dry yeast which not only exhibits a high leavening activity when employed in its intended, direct addition manner, but which also exhibits a comparably high leavening activity even if used in a manner in which it is separately rehydrated prior to admixture with remaining dough or batter ingredients.

Another object of the invention is to provide an instant-type active dry yeast having the foregoing characteristics utilizing procedures and materials which are cost-effective and which are easy to implement in existing yeast manufacturing processes.

According to the present invention, an instant-type active dry yeast is provided which possesses a leavening activity, measured in direct addition tests described in further detail hereinafter, of at least about 1000 (cc of $CO_2$ evolved), and closely comparable values when the leavening activity is measured in tests wherein the yeast is first rehydrated in water.

In order to express the relationship between the direct addition and rehydration activities, rehydration of the yeast in water at both 70° F. and 110° F. are employed. The activity of the yeast as measured in direct addition is referred to as "$A_{DA}$" while the leavening activity of the yeast as measured in methods involving rehydration in 70° F. water and 110° F. water are referred to, respectively, as "$A_{70}$" and "$A_{110}$". Using the foregoing terminology, the instant-type active dry yeast of the present invention possesses a leavening activity such that the values for $A_{70}/A_{DA}$ and $A_{110}/A_{DA}$ are at least about 0.88 and, preferably, at least about 0.90. In addition, the value of $A_{70}/A_{110}$ preferably is above about 0.90, and most preferably above 0.92.

An instant-type active dry yeast possessing these characteristics comprises a yeast which is of a suitable strain and which has been dried in a manner which produces a dry yeast having a leavening activity—measured by direct addition methods—of at least about 1000 (cc of $CO_2$ evolved), and which further comprises from about 0.1% to about 2.0% (dry matter basis) of a material selected from the group consisting of locust bean gum, gum ghatti and mixtures thereof.

In the process of the present invention, yeast (typically in the form of compressed yeast or a clarified/filtered yeast suspension) is dried under mild drying conditions, the particular yeast strain, propagation process, drying techniques and conditions being chosen so as to provide an instant-type active dry yeast having a moisture content of about 10% or less and a leavening activity—when measured in direct addition tests—of at least about 1000 (cc of $CO_2$ evolved). The instant-type active dry yeast as above-described further comprises from about 0.1% to about 2.0% by weight (dry matter basis) of a material selected from the group consisting of locust bean gum, gum ghatti and mixtures thereof. This material typically will be admixed with the yeast prior to the drying process, but may, in whole or in part, also be mixed with the yeast at other points in the overall process.

The instant-type active dry yeast of the invention possesses comparable, excellent leavening activity whether employed in direct addition with flour and other dough or batter ingredients or in processes wherein it is first rehydrated in water, or other aqueous medium, prior to its mixture with remaining dough or batter ingredients. As a consequence, the instant-type active dry yeast of the invention is ideally suited for use in current day commercial and consumer environs since it provides a high degree of tolerance against potential poor leavening results encountered by those persons who, despite the deliberate manufacture of the yeast to provide high activity in direct addition processes, nevertheless use the product by first rehydrating it.

BACKGROUND ART

As earlier noted, it is known in the art to conduct the drying of yeast in the presence of one or more lipophilic surfactants in order to protect the yeast cells from damage as low moisture contents are approached.

In the preparation of active dry yeasts, the use of particular gums also is known. For example, in Canadian Pat. No. 1,075,077, the drying of yeast is performed in the presence of "emulsifying" and "stabilizing" agents having film forming properties suitable for protecting the yeast during drying and for facilitating its reconstitution. Prior to drying there is added to the yeast an emulsion in water of sorbitol ester, or of lactic ester, or of diacetyl tartaric ester of mono and diglycerides, or of a stearoyl-2-lactylate of sodium or calcium and of gum arabic, or of guar gum or of carragheenate. The emulsifying agent is used at a level of 0.5 to 2.0% of the finished dried product and the agent stabilizing the emulsion is used at a level of 0.5 to 1.0% of the finished product. This same disclosure is found in U.S. Pat. No. 4,328,250. In U.S. Pat. No. 4,346,115, drying is done in the presence of "emulsifying and stabilizing agents with suitable emulsifying and film-forming properties" (emulsion of sorbitol ester and gum arabic specifically disclosed), while U.S. Pat. Nos. 4,318,930 and 4,396,632 refer to use of an emulsifying agent (sorbitol esters, polyglycerol esters) and a "thickening" agent.

U.S. Pat. Nos. 3,843,800 and 4,217,420 disclose that a "swelling agent and/or a wetting agent" preferably is mixed with the yeast suspension prior to drying to the desired low moisture content. The disclosed swelling agents, used in amounts from 0.5 to 5.0% (dry matter basis), are methyl cellulose and carboxymethyl cellulose, and the disclosed wetting agents, also used in amounts from 0.5 to 5.0% (dry matter basis), are esters of saturated fatty acids, fatty acid esters of glycerol, fatty acid esters of propylene glycol or mixtures thereof.

To the extent the foregoing patents relate to instant-type active dry yeast, their testing of yeast leavening properties all, of course, involve direct addition methods of utilization. In accordance with the present invention, a number of significant findings have been made which have not been considered or addressed by previous art workers. While gums have been employed in prior active dry yeast processes, little is understood by previous workers regarding the role and effect thereof. For example, in the U.S. Pat. Nos. 3,843,800 and 4,217,420, dealing with dried yeasts which can have moisture contents as low as 4%, the use of a wetting agent (e.g., particular lipophilic surfactant) and the use of a swelling agent (i.e., methyl cellulose, carboxymethyl cellulose) are contemplated both alternatively and in concert ("the yeast of the invention preferably contains a swelling agent and/or a wetting agent"; see also Example IX(9) of both patents where a swelling agent alone is used, the remaining examples using a wetting agent alone). However, contrary to the teaching of these patents, for production of yeasts having a moisture content below about 6.5% to 7%, use of a lipophilic surfactant wetting agent is essential for protecting the yeast cell membrane from damage. In other of the earlier-noted patents, utilization of emulsifying agents (cf. wetting agents) and "stabilizers" or "thickening" agents (e.g., gum arabic, carraghenate, guar gum) has reference to "protecting the yeast during drying" and for "facilitating its reconstitution". In conventional active dry yeasts, which require separate rehydration in order to develop their activity, gums can be used to control the rate of rehydration thereby preventing undue damage to the yeast cells as they are confronted with an activating medium devoid of essential nutrients. For instant-type active dry yeasts, however, perhaps as a result of their fine particle size, generally lower initial moisture, particular yeast strain for obtaining high direct addition activity or other factors, separate rehydration has been found to lead to significant cell damage and consequent poor leavening activity when thereafter mixed with remaining dough ingredients. A number of the materials taught by the prior art for assisting rehydration of yeasts specifically manufactured for utilization in rehydration methods are ineffective for similarly assisting rehydration of instant-type active dry yeasts.

DETAILED DESCRIPTION OF THE INVENTION

As used throughout the description of the invention, the "leavening activity" of a particular yeast is measured according to a straight dough procedure as follows.

The dry mix of dough ingredients is formulated as follows:

Domestic Bread Flour: 150 grams
Sugar: 9 grams
Salt: 3 grams
Non-Fat Dry Milk: 4.5 grams
Malt: 1.50 grams
Bromate/Ammonium salt (yeast food): 0.75 grams
Calcium Propionate: 0.19 grams In this mix, the flour is any good quality domestic bread flour such as Peavey Occident; the salt is any granulated Bakers' salt; the sugar is any fruit granulated sugar; the yeast food is any bromate/ammonium salt yeast food similar to ADM Arkady; and the malt is a dry malt syrup 20° Lintner (such as that sold as Diamalt).

This dry mix is placed in a dough mixer with 4.5 grams of a plastic shortening and mixed for one minute. The shortening is any good quality plastic shortening such as MFB sold by Hunt-Wesson, Inc. The mixer is a bench-size dough mixer capable of handling 100-160 gram batches, such as that sold by National Equipment Co. Water is then added to obtain a uniform dough consistency (generally this will require addition of about 100±5 cc water; as discussed below, for direct addition tests, the entire amount of this water is added at this stage; for rehydration tests, a portion of this total added water is used for rehydration and for rinsing the rehydration vessel). Mixing is continued for one minute, after which the dough is scraped down and the yeast added. Time is recorded at this point as "time zero38 (TO). The dough is further mixed for 5 minutes and removed from the mixer. The dough temperature at this point is recorded and should be about 86° F. (30° C.). The dough ball is placed in a lightly greased bread pan and placed in a fermentation recorder (a jacketed and thermostated proofing chamber, gas collection chamber and means for reading volume changes, such as the SJA Fermentation Recorder sold by AB Nassjo Metallverkstad of Sweden). At TO plus 10 minutes, the recorder chamber is sealed and gas collected for 90 minutes (fermentation values). The dough ball is then removed, sheeted and returned to the recorder (reset to zero baseline). Gas is again collected, this time for 60 minutes (proof values). The values for the gaseous volumes (in cc of evolved $CO_2$) for the 90 and 60 minute periods are combined and corrected for any necessary calibration factors for the recorder and for reporting the values at 30° C., 760 mm Hg.

In direct addition tests, the dry yeast (1.80 grams) is simply sprinkled on the dough in the mixer. In rehydration tests, the yeast is sprinkled on 7.5 cc of water at the appropriate temperature (e.g., at 70° F. or 110° F.) and allowed to stand for 7 minutes. The yeast and water are then mixed to form a uniform dispersion, and allowed to stand for another 3 minutes. The rehydrated yeast is then added to the mixed dough as described above, the rehydration vessel is washed with 10 cc water, and that too is then added to the mixed dough for continuation of mixing, etc. as above-noted.

An alternative method for measuring yeast activity also has been employed which can increase the rate at which samples can be processed. This method, which via empirically derived correlation equations is designed to yield activity values closely approximating those which would be obtained if the more time-consuming procedure described above were used, is as follows:

In addition to the equipment set forth above, a fermentation chamber or cabinet also is employed. This is a chamber in which several bread pans can be placed and which is capable of maintaining a fixed temperature and humidity. A suitable apparatus is available from National Equipment Co. of Lincoln, Neb.

In practice, the dough is prepared as in the earlier-noted procedure (for both direct addition and rehydration methods). After mixing, the dough is removed from the mixer bowl and, as in the previous method, the dough temperature measured and recorded (and should be about 86° F.). The dough ball is placed in a lightly greased bread pan and placed in the fermentation cabinet (rather than into the fermentation recorder as in the previous method) maintained at 30° C., 90% RH. In contrast to the earlier procedure, no measurement of evolved gas is conducted while the dough is in this fermentation cabinet. At TO (time zero, as defined in the previous method) plus 100 minutes, the dough ball is removed from the fermentation cabinet, sheeted and then placed in the fermentation recorder where gas is collected for sixty minutes (proof values). The quantity of gas collected is recorded and corrected for any necessary calibration factors and for reporting values at 30° C., 760 mm Hg.

To determine total activity (gas evolved during combined fermentation and proof, in cc) based on actual measurement only of proof values, the following empirically derived equations are employed (which differ depending upon the method of yeast addition):

Direct Addition: Total=Proof value×1.76+26.5
Rehydration (110° F.): Total=Proof value×2.05−162
Rehydration (70° F.): Total=Proof value×1.96−112

When reference is made herein to a particular yeast leavening activity, therefore, such activity is that as measured by either of the foregoing procedures. For case of reference, these procedures are coined "EVM Straight Dough Procedure."

According to the present invention, an instant-type active dry yeast is prepared by processes which, with the exception of the presence of locust bean gum, gum ghatti or mixtures thereof according to the invention, are essentially as known in the art. The final instant-type active dry yeast to be obtained has a moisture content below about 10%, preferably below about 6%, and generally from about 3 to 5% by weight, and a leavening activity, measured in direct addition tests, of at least about 1000 cc. Through practice of the invention, such a yeast further has a leavening activity, measured in tests where the yeast is separately rehydrated before admixture with the remaining dough ingredients, on the order of at least about 88% to 90% of that measured in direct addition tests.

In commercial processes for propagating yeast, it is common practice to proceed by stages. Generally, propagation is started by inoculation of yeast into a presterilized nutrient medium usually contained in a shaker flask. In the flask, growth of the yeast is encouraged by various means, e.g., shaking for aeration and maintenance of suitable temperature. The yeast is removed from the flask and inoculated into another flask containing a larger volume of nutrient medium and growth of the yeast induced. These initial stages may conveniently be referred to as flask or culture development stages. From these stages the yeast may be inoculated into a vessel having an air source and means of agitation. The steps or stages may be repeated once or twice using greater amounts of nutrient in medium and larger vessels. Because the amount of air used in these stages is generally restricted, these stages are commonly referred to as slightly aerobic stages. Yeast from these stages is then transferred into larger fermentors where vigorous growth conditions are maintained, including the use of large volumes of air. These stages may be referred to as highly aerobic or commercial stages since the yeast from these stages is harvested and processed for bakery use. Non-nutritive salts may be added in the final propagation stages to increase the leavening activity of the yeast in accordance with the process set forth in U.S. Pat. No. 3,617,306.

The strain of yeast (or combined strains of yeast) employed in the propagation process will be selected from those yeast strains which, as known in the art, are particularly well suited to the preparation of active dry yeast in general and instant-type active dry yeast in particular, by reason of their hardiness and metabolic stability which enables them to be dried to a low moisture content without severe adverse effect on their leavening activity. Exemplary yeast strains for use in the present invention are those of BN 23 (see Schultz and Atkin, Archives of Biochemistry, 14: 369–380, 1947).

After propagation, the yeast is separated from the other constituents of the growth medium, washed and centrifuged several times. The yeast at this point in the process is known in the art as yeast cream. The yeast cream is then transferred to a filter where a relatively large quantity of the water is removed. Typically, the yeast cream will be treated with an aqueous solution of, e.g., a salt such as sodium chloride, to force water (by osmotic action) from the cells of the yeast prior to the filtration. During filtration, the yeast is washed with water to remove excess salt. The yeast obtained at this point in the processing is referred to as compressed yeast and contains about 30% yeast solids by weight.

The compressed yeast is then subjected to drying to reduce its moisture content to a suitably low level appropriate for an instant-type active dry yeast, i.e., 10% by weight or below, and most typically below about 6% by weight. As noted at the outset, where the final moisture content of the yeast is to be below about 8%, it generally will be necessary to perform the drying process in the presence of a lipophilic surfactant or wetting agent to prevent damage to the yeast during drying. Particularly preferred surfactants, generally employed at a level of from about 0.5 to 2.0% by weight (dry matter basis), are sorbitan fatty esters such as sorbitan monolaurate, monostearate, monopalmitate and monooleate and the like; glycerol fatty acid esters such as the monostearate, monopalmitate, distearate and the like, as well as esters with lower organic acids such as acetic acid, lactic acid, citric acid, tartaric acid, diacetyltartaric acid and the like; and propylene glycol fatty acid esters such as propylene glycol monostearate; and mixtures of two or more such compounds.

In accordance with the present invention, the final yeast product contains from about 0.1 to about 2.0% by weight (dry matter basis) of locust bean gum, gum ghatti or a combination thereof in order to produce an instant-type active dry yeast having high direct addition activity and comparably high rehydration activity (i.e., the latter being at least about 88 to 90% of the former). These materials may be added to the compressed yeast prior to drying and/or may be included with the yeast at some other convenient point in the overall process. Where a lipophilic surfactant also is to be employed, it generally will be desirable to form an admixture of the gum and such surfactant in water (along with any other materials which are sought to be included in the final yeast product), and then add this pre-formed mixture to the yeast prior to extrusion and drying.

The drying of the yeast is accomplished by methods generally employed in the art. Such methods typically involve extruding the compressed yeast through an appropriate die to produce strands of material (the so-called "spaghetti process" of U.S. Pat. No. 3,617,306) which are then subjected to drying under controlled conditions. For example, the strands can be extruded and then dried in a fluidized bed dryer, in one or a plurality of stages, or on a moving conveyor belt which carries the strands through a number of drying zones maintained at temperatures effective for controlled drying to the requisite moisture level. The temperature and residence time are adjusted as known in the art so that the moisture level of the yeast is efficiently reduced to the desired level without causing excessive reduction in yeast activity.

As is characteristic of instant-type active dry yeasts, the dry yeast of the present invention will have a relatively fine particle size. Generally, less than about 10% of the particles will be retained on a No. 30 U.S. Standard Sieve Screen as determined in a standard particle size classification/screen analysis, using a Tyler Ro-Tap sifter, U.S. Standard sieves vertically stacked in order of fineness (coarsest sieve at top) and a shaking time of 10 minutes (using the knocker arm, provided with the Ro-Tap sifter, which is in contact with a cover over the uppermost screen). A typical particle size distribution for such a yeast is as follows: percent by weight retained on No. 30 sieve - 5%; percent by weight retained on No. 40 sieve - 45%; percent by weight retained on No. 50 sieve - 48%; percent by weight retained on No. 60 sieve - 2%.

The following examples describe the manner and process of making and using the invention and the best mode contemplated by the inventors of carrying out the invention, but are not intended to be taken as limiting the otherwise stated scope of the invention.

EXAMPLE I

A yeast cream obtained from propagation of a yeast strain of BN 23 was dewatered in a filter press, and into the resultant yeast filter cake were incorporated 0.25% of locust bean gum, 1.0% sorbitan monostearate, 0.9% oil and 0.1% butylated hydroxyanisole, all percents by weight, dry matter basis. The yeast filter cake was then extruded into spaghetti-like strands and dried, in a fluidized bed dryer over the course of about 2 hours, to a final moisture content of about 4.0 to 5.0% by weight.

In tests of the leavening activity of the yeast so produced, using the direct addition and rehydration methods set forth earlier herein, a direct addition value ($A_{DA}$) (average six runs) of 1427 cc was obtained while values for rehydration leavening activity, using rehydration water at 70° F. and 110° F., were 1372 cc and 1402 cc, respectively (average of six runs each). Thus, the ratios for $A_{70}/A_{DA}$ and $A_{110}/A_{DA}$ were 0.96 and 0.99, respectively, and the ratio of $A_{70}/A_{110}$ was 0.98.

EXAMPLE II

Following the identical processing conditions, yeast strain and additives (other than locust bean gum) as set forth in Example I, an instant-type active dry yeast was prepared containing 0.25% by weight, dry matter basis, of gum ghatti. Leavening activity in direct addition tests resulted in a value of 1367 cc, while leavening activity after prior rehydration in 70° F. and 110° F. water was 1243 cc and 1256 cc, respectively. Thus, the values of $A_{70}/A_{DA}$ and $A_{110}/A_{DA}$ were 0.91 and 0.92, respectively, and the value of $A_{70}/A_{110}$ was 0.99.

EXAMPLE III

Following the preparation and testing set forth in Example I, an instant-type active dry yeast was prepared containing 0.25% by weight (dry matter basis) of carrageenan in place of locust bean gum. The leavening activity in direct addition tests was 1372 cc and the leavening activity after prior rehydration in 70° F. and 110° F. water was 1062 cc and 1249 cc, respectively. Thus, the value of $A_{110}/A_{DA}$ was 0.91; however, the value of $A_{70}/A_{DA}$ was 0.77. The value of $A_{70}/A_{110}$ was 0.85.

The foregoing examples illustrate the distinct advantage of the present invention in providing what is essentially a "foolproof" instant-type active dry yeast which possesses a high leavening activity regardless of its method of use. Additive materials which provide a yeast having a desirable leavening activity in direct addition processes as well as in rehydration processes using 110° F. water, but which do not similarly provide comparable activity at other rehydration temperatures (e.g., 70° F.), are not useful for purposes of the present invention since the yeast product does not provide "across-the-board" excellent activity; in such circumstances, the potential for poor results and consumer disappointment exists.

What is claimed is:

1. An instant active dry yeast containing from about 0.1 to about 2.0% by weight, dry matter basis, of a material selected from the group consisting of locust bean gum, gum ghatti and mixtures thereof, said instant active dry yeast having a moisture content of about 10% or less by weight, a leavening activity of at least about 1000 cc of evolved $CO_2$ when measured in tests wherein said yeast is added directly to flour and other dough or batter ingredients without prior rehydration of the yeast, and a leavening activity, when measured in tests in which said yeast is separately rehydrated in 70° F. and 110° F. water prior to admixture with flour and other dough or batter ingredients, of at least about 88% of the leavening activity of said yeast when measured in tests wherein said yeast is directly added to flour and other dough or batter ingredients without prior yeast rehydration, said leavening activities herein having reference to leavening activity, in cc of evolved $CO_2$ as determined by an EVM Straight Dough Procedure.

2. An instant active dry yeast according to claim 1 further containing from about 0.5 to about 2.0% by weight, dry matter basis, of a lipophilic surfactant.

3. An instant active dry yeast according to claim 2 wherein said surfactant is an ester of a saturated or unsaturated fatty acid.

4. An instant active dry yeast according to claim 2 wherein said surfactant is selected from the group consisting of sorbitan fatty esters, glycerol fatty acid esters, propylene glycol fatty acid esters, and mixtures thereof.

5. An instant active dry yeast according to any of claims 2, 3 or 4 wherein the moisture content of said yeast is about 6% or less.

6. An instant active dry yeast according to claim 1 having a particle size distribution such that less than about 10% of the particles are retained on a No. 30 U.S. Standard Sieve Screen.

7. In a process for preparing an instant active dry yeast wherein a yeast cream, obtained from a yeast strain selected for its ability to be dried without substantial adverse affect on its leavening activity when employed in a manner wherein the instant active dry yeast is directly added to flour and other dough or batter ingredients without prior yeast rehydration, is dewatered and then subjected to mild controlled drying conditions to produce a yeast having a moisture content of about 10% or less by weight and a leavening activity of at least about 1000 cc of evolved $CO_2$ when measured in tests wherein said yeast is directly added to flour and other dough or batter ingredients without prior yeast rehydration, the improvement comprising conducting said drying in the presence of a material selected from the group consisting of locust bean gum, gum ghatti and mixtures thereof, admixed with the yeast in an amount sufficient to provide from about 0.1 to about 2.0% thereof by weight, dry matter basis, in said instant active dry yeast, whereby the leavening activity of said instant active dry yeast, when measured in tests wherein said yeast is separately rehydrated in 70° F. and 110° F. water prior to admixture with flour and other dough or batter ingredients, is at least about 88% of the value of the leavening activity of said yeast when measured in tests wherein said yeast is directly added to flour and other dough or batter ingredients without prior yeast rehydration, said leavening activities herein having reference to leavening activity, in cc of evolved $CO_2$, as determined by an EVM Straight Dough Procedure.

8. The process according to claim 7 wherein said drying is further conducted in the presence of a lipophilic surfactant.

9. The process according to claim 8 wherein said surfactant is an ester of a fatty acid.

10. The process according to claim 9 wherein said surfactant is selected from the group consisting of sorbitan fatty esters, glycerol fatty acid esters, propylene glycol fatty acid esters, and mixtures thereof.

11. The process according to claim 10 wherein said surfactant is sorbitan monostearate.

12. The process according to any of claims 8, 9, 10 or 11 wherein the moisture content of said instant active dry yeast is about 6% or less.

* * * * *